United States Patent [19]

Löher et al.

[11] Patent Number: 5,536,698
[45] Date of Patent: Jul. 16, 1996

[54] CROP-PROTECTING COMPOSITIONS CONTAINING ISOXAZOLINES OR ISOTHIAZDINES, NOVEL ISOXAZOLINES, AND THEIR PREPARATION

[75] Inventors: Heinz-Josef Löher, Liederbach; Klaus Bauer, Hanau; Hermann Bieringer, Eppstein/Taunus, all of Germany

[73] Assignee: Hoechst Aktiengesellschaft, Frankfurt, Germany

[21] Appl. No.: 467,934

[22] Filed: Jun. 6, 1995

Related U.S. Application Data

[63] Continuation of Ser. No. 233,612, Apr. 19, 1994, abandoned, which is a continuation of Ser. No. 867,966, Apr. 13, 1992, abandoned.

[30] Foreign Application Priority Data

Apr. 15, 1991 [DE] Germany .................. 41 12 251.8

[51] Int. Cl.$^6$ .................................................. A01N 25/32
[52] U.S. Cl. .................................................. 504/106
[58] Field of Search .................................................. 504/106

[56] References Cited

U.S. PATENT DOCUMENTS

| | | | |
|---|---|---|---|
| 4,877,881 | 10/1989 | Belliotti et al. | 548/240 |
| 4,889,551 | 12/1989 | Oda et al. | 71/88 |

FOREIGN PATENT DOCUMENTS

| | | |
|---|---|---|
| 0152006 | 2/1989 | European Pat. Off. |
| 0174562 | 1/1991 | European Pat. Off. |
| 4026018 | 2/1992 | Germany |
| WO91/08202 | 6/1991 | WIPO |

OTHER PUBLICATIONS

K. Harada et al., Chem. Pharm. Bull., vol. 28, No. 11, (1980), p. 3296 ff.
A. P. Kozikowski et al., J. Org. Chem., vol. 48, (1983), p. 366 ff.
H. Suzuki et al., Chem. Letters, vol. 4, (1990), p. 559 ff.
A. Hassner et al., J. Org. Chem., vol. 54, (1989), p. 5277 ff.
S. Auricchio et al., Tetrahedron Letters, vol. 43, No. 17, (1987), p. 3983 ff.
P. Caldirola et al., Tetrahedron Letters, vol. 42, No. 19, (1986), p. 5267 ff.
T. Shimizu et al., Bull. Chem. Soc. Jpn., vol. 59, (1986), p. 2827 ff.
T. Shimizu et al., Bull. Chem. Soc. Jpn., vol. 58, (1985), p. 2519 ff.
J. Kalvoda et al., J.C.S. Chem. Comm., vol. 6, (1976), p. 209 ff.
G. S. King et al., J.C.S. Perkin I, vol. 1, (1972), p. 437 ff.
Journal of Organic Chemistry, vol. 25, Nr. 7, 8. Jul. 1960, Easton US, pp. 1160–1164, Wyman R. Vaughan et al., "5–Phenyl–2–isoxazoline–3–carboxylic acid".
Synthesis, Jun. 6, 1986, Stuttgard DE, pp. 488–490, Tomio Shimizu et al., "Synthesis of isoxazoline–3–carboxanilides and isoxazole–3–carboxanilides by thermolysis of alpha--methoxycarbonyl–alpha nitroacetanilides in the presence of dipolarophiles".
Tetrahedron, vol. 41, Nr. 4, 1985, Oxford GB, pp. 727–738, Tomio Shimizu et al., "Reaction of 3, 4–disubstituted 1, 2, 5–oxadiazole 2–oxides with dipolarophiles".

*Primary Examiner*—José G. Dees
*Assistant Examiner*—Brian Bembenick
*Attorney, Agent, or Firm*—Curtis, Morris & Safford

[57] ABSTRACT

Crop-protecting compositions containing isoxazolines or isothiazolines, novel isoxazolines and isothiazolines, and their preparation Crop-protecting compositions which contain isoxazolines or isothiazolines of the formula in which X is oxygen or sulfur, R is hydroxyl or has the meanings given in the description, Z is halogen, nitro, cyano, in each case optionally substituted alkyl, alkoxy, alkylmercapto, cycloalkyl, amino, hydroxymethyl, alkylamino, dialkylamino, alkoxymethyl, aryl or aryloxy and n is an integer from 0 to 5. Novel isoxazolines and isothiazolines of this formula, a process for their preparation, and their use as a protection against phytotoxic secondary effects of herbicides.

17 Claims, No Drawings

CROP-PROTECTING COMPOSITIONS CONTAINING ISOXAZOLINES OR ISOTHIAZDINES, NOVEL ISOXAZOLINES, AND THEIR PREPARATION

This application is a continuation of U.S. patent application Ser. No. 08/233,612, filed Apr. 19, 1994 (abandoned) which is a continuation of U.S. patent application Ser. No. 07/867,966, filed Apr. 13, 1992 (abandoned).

The use of herbicides can result in undesired, unacceptable damage to crop plants. There is therefore frequently the need to avoid the risk of a potential phytotoxicity, in particular when herbicides are applied after emergence of the crop plants.

Such compounds which have the property of protecting crop plants against phytotoxic damage by herbicides without impairing the actual herbicidal effect of the compositions are termed "antidotes" or "safeners".

A range of compounds has already been described for this application (cf., for example, EP-A-152,006 or EP-A-174,562).

The use of certain isoxazolines and isothiazolines as safeners has been proposed in German Patent Application P 40 26 018.6 (HOE 90/F 251).

The invention relates to compositions which protect crop plants and which contain isoxazolines or isothiazolines of the formula I or salts thereof,

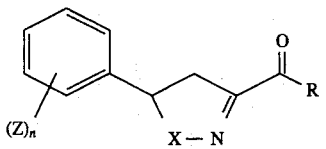

(I)

in which

X is an oxygen or sulfur atom, in particular an oxygen atom,

R is a) hydroxyl, mercapto, alkoxy, alkenyloxy, alkynyloxy, alkylmercapto, alkenylmercapto, alkynylmercapto, cycloalkyloxy or cycloalkylmercapto, the last 8 groups mentioned being unsubstituted or substituted by one or more, preferably up to three, identical or different radicals selected from the group comprising aryl, alkoxy, alkenyloxy, alkynyloxy, aralkyloxy, aryloxy, cycloalkyloxy, alkylmercapto, mono- or dialkylamino, cyano, halogen and nitro, b) aralkyloxy, aryloxy, aralkylmercapto or arylmercapto, each of which is unsubstituted or substituted by one or more, preferably up to five, identical or different radicals selected from the group comprising alkyl, alkenyl, alkynyl, halogen, cyano, nitro, alkoxy, alkenyloxy, alkynyloxy, alkylmercapto, mono- or dialkylamino, aryloxy and aroyloxy, or is trialkylsilylalkoxy, aryldialkylsilyloxy, aralkyldialkylsilyloxy, diarylalkylsilyloxy or diaralkylalkylsilyloxy, c) a radical of the formula NR'R', R' being identical or different radicals selected from the group comprising hydrogen, alkyl, alkenyl, alkynyl and cycloalkyl, or is pyridino, morpholino, dialkylmorpholino, hydrazino or a radical of the formula

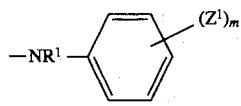

in which $R^1$ is hydrogen, alkyl, alkenyl or alkynyl, the radicals $Z^1$ independently of one another are halogen, nitro, alkyl, alkenyl, alkoxy or aryloxy and m is an integer from 0 to 5, d) a radical of the formula

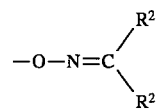

in which the radicals $R^2$ independently of one another are alkyl or together with the carbon atom linking them are cycloalkylidene, e) a radical of the formula $—O—CR^3R^3—CO—R^4$ in which $R^3$ radicals are identical or different radicals selected from the group comprising hydrogen, alkyl, alkenyl, alkynyl, aryl, aralkyl, alkoxy, alkenyloxy, alkynyloxy and aryloxy and $R^4$ is hydrogen, alkyl, alkenyl, alkynyl, aryl or aralkyl, f) a radical of the formula

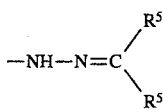

in which $R^5$ is identical or different radicals selected from the group comprising hydrogen, alkyl and aryl, or the two radicals $R^5$ together with the carbon atom linking them are cycloalkylidene, or g) a radical of the formula $—O—CR^6R^6—CO—R^7$ in which $R^6$ radicals are identical or different radicals selected from the group comprising hydrogen, alkyl, alkenyl, alkynyl, aryl, aralkyl, alkoxy, alkenyloxy, alkynyloxy and aryloxy, and $R^7$ has one of the meanings given above for R under a) to f), Z is halogen, nitro, cyano, $(C_1–C_4)$-alkyl, $(C_1–C_4)$alkoxy, $(C_1–C_4)$-alkylmercapto, the alkyl, alkoxy and alkylmercapto groups independently of one another in each case being unsubstituted or substituted by one or more, preferbly up to 6, halogen atoms, in particular fluorine or chlorine, or is $(C_3–C_6)$-cycloalkyl which is unsubstituted or substituted by preferably up to three $(C_1–C_4)$-alkyl radicals, amino, hydroxymethyl, $(C_1–C_4)$-alkylamino, di-$(C_1–C_4)$-alkylamino, $(C_1–C_4)$-alkoxymethyl, the alkyl and alkoxy groups in the last three radicals mentioned independently of one another being unsubstituted or substituted by preferably up to three $(C_1–C_4)$-alkyl radicals, or aryl or aryloxy, aryl and aryloxy independently of one another in each case being unsubstituted or mono- or polysubstituted, preferably by up to five identical or different radicals selected from the group comprising halogen and trifluoromethyl, and n is an integer from 0 to 5, in particular 0 to 3, and conventional formulation auxiliaries.

The invention furthermore relates to selective herbicidal compositions which contain an active substance of the abovementioned formula I or salts thereof in combination with a herbicide and, if appropriate, customary formulation auxiliaries.

In formula I, the alkyl, alkenyl and alkynyl radicals can in each case be straight-chain or branched. They have preferably up to five carbon atoms. The same applies analogously to the radicals derived from the above radicals, such as alkoxy, alkylmercapto, alkylamino, dialkylamino and the corresponding unsaturated radicals.

Cycloalkyl radicals and radicals derived therefrom such as cycloalkyloxy or cycloalkylmercapto have preferably 3 to 7 carbon atoms.

Aryl radicals have preferably 6 to 12 carbon atoms; preferred radicals are phenyl, naphthyl and biphenyl, in particular phenyl. The same applies analogously to radicals derived therefrom such as aryloxy, arylmercapto, aroyl, aralkyl, aralkyloxy and aralkylmercapto. Aralkyl is preferably benzyl.

Halogen is fluorine, chlorine, bromine or iodine, preferably fluorine, chlorine or bromine, in particular fluorine or chlorine.

In the case where R is hydroxyl, the compounds of the formula I can form salts. Salts which can be employed according to the invention are those which can be used in agriculture. Examples of suitable salts are metal salts such as alkali metal salts or alkaline earth metal salts, in particular sodium salts or potassium salts, or salts with ammonium, mono-, di-, tri- or tetra-$(C_1-C_4)$-alkylammonium or with mono-, di-, tri- or tetra-$(C_1-C_4)$-alkanolammonium.

In particular, the invention also relates to all stereoisomers and mixtures thereof which are embraced by the formula I but not defined specifically. Stereoisomers can occur especially if one or more asymmetric carbon atoms and/or suitably substituted double bonds exist in the compounds of the formula I. The stereoisomers can be obtained from racemic mixtures by customary separation methods. Alternatively, stereoisomers can be prepared selectively by using stereoselective reactions and optically active starting materials or auxiliaries.

Particularly interesting crop-protecting or selective herbicidal compositions according to the invention are those which contain a compound of the abovementioned formula I in which R is a) hydroxyl, mercapto, $(C_1-C_4)$-alkoxy, $(C_2-C_4)$-alkenyloxy, $(C_2-C_4)$-alkynyloxy, $(C_1-C_4)$-alkylmercapto, $(C_2-C_4)$-alkenylmercapto, $(C_2-C_4)$-alkynylmercapto or $(C_3-C_8)$-cycloalkylmercapto, the last 8 groups mentioned being unsubstituted or substituted by one or more, preferably up to three, identical or different radicals selected from the group comprising aryl, $(C_1-C_4)$-alkoxy, $(C_2-C_4)$-alkenyloxy, $(C_2-C_4)$-alkynyloxy, aralkyloxy, aryloxy, $(C_3-C_8)$-cycloalkyloxy, $(C_1-C_4)$-alkylmercapto, mono- or di-$(C_1-C_4)$-alkylamino, cyano, halogen and nitro, b) aryloxy, arylmercapto, aralkyloxy or aralkylmercapto, each of which is unsubstituted or substituted by one or more, preferably up to five, identical or different radicals selected from the group comprising $(C_1-C_4)$-alkyl, $(C_2-C_4)$-alkenyl, $(C_2-C_4)$-alkynyl, halogen, cyano, nitro, $(C_1-C_4)$-alkoxy, $(C_2-C_4)$-alkenyloxy, $(C_1-C_4)$-alkynyloxy, $(C_1-C_4)$-alkylmercapto, mono- or di-$(C_1-C_4)$-alkylamino, aryloxy and aralkyloxy, or is tri-$(C_1-C_4)$-alkylsilylalkoxy, c) a radical of the formula —NR'R' in which R' is hydrogen and/or $(C_1-C_4)$-alkyl, pyridino, morpholino, dimethylmorpholino, hydrazino or a radical of the formula

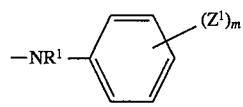

in which $R^1$ is hydrogen or $(C_1-C_4)$-alkyl, the radicals $Z^1$ independently of one another are halogen, nitro, $(C_1-C_4)$-alkyl, $(C_1-C_4)$-alkoxy or aryloxy and m is 0 to 3, d) a radical of the formula —O—N=$CR^2R^2$ in which $R^2$ is $(C_1-C_4)$-alkyl, in particular methyl, or the radicals $R^2$ together with the carbon atom linking them are cyclohexylidene or cyclopentylidene, e) a radical of the formula —O—$CR^3R^3$—CO—$R^4$ in which $R^3$ radicals are identical or different radicals selected from the group comprising hydrogen, $(C_1-C_4)$-alkyl, $(C_2-C_4)$-alkenyl, $(C_2-C_4)$-alkynyl, aryl, aralkyl or $(C_1-C_4)$-alkoxy and $R^4$ represents $(C_1-C_4)$-alkyl, $(C_2-C_4)$-alkenyl, $(C_2-C_4)$-alkynyl, aryl or aralkyl, f) a radical of the formula —NH—N=$CR^5R^5$ in which $R^5$ radicals are identical or different radicals selected from the group comprising hydrogen, $(C_1-C_4)$-alkyl or aryl, or the two radicals $R^5$ together with the carbon atom linking them are cyclohexylidene or cyclopentylidene, or g) a radical of the formula —O—$CR^6R^6$—CO—$R^7$ in which $R^6$ radicals are identical or different radicals selected from the group comprising hydrogen, $(C_1-C_4)$-alkyl, $(C_2-C_4)$-alkenyl, $(C_2-C_4)$-alkynyl, aryl, aralkyl and $(C_1-C_4)$-alkoxy, and $R^7$ has one of the meanings given above for R under a) to f).

Particularly preferred compositions are those in which, in formula I, R is hydrogen, $(C_1-C_4)$-alkoxy, $(C_2-C_4)$-alkenyloxy, $(C_2-C_4)$-alkynyloxy, benzyloxy, phenyloxy, NR'R' with R'=hydrogen and/or $(C_1-C_4)$-alkyl, hydrazino or —O—$CR^3R^3$—CO—$R^4$ with $R^3$=hydrogen and $R^4$=$(C_1-C_4)$-alkoxy, Z radicals are identical or different radicals selected from the group comprising halogen, in particular fluorine and/or chlorine, $(C_1-C_4)$-alkyl and $(C_1-C_4)$-alkoxy, and n is 0, 1 or 2.

Some compounds of the formula I where $(Z)_n$=hydrogen and R=—$OCH_3$, —$OC_2H_5$, —O—$CH_2$—CH=CH—$C_6H_5$, —$OCH_2$CH=$CHCH_3$ and —$OCH_2CH_2$CH=$CHCH_3$ and processes for their preparation are known from the literature, but their safener action was not recognized; cf., for example, Chem. Pharm. Bull. 28, 3296 (1980); J. Org. Chem. 25, 1160 (1960); J. Org. Chem. 48, 366 (1983); Chem. Lett. 4,559 (1990); J. Org. Chem. 54, 5277 (1989); Tetrahedron 43, 3983 (1987); Tetrahedron 42, 5267 (1986); Bull. Chem. Soc. Japan 59, 2827 (1986); Bull. Chem. Soc. Japan 58, 2519 (1985); J. Chem. Soc., Chem. Commun. 6, 209 (1976); J. Chem. Soc., Perkin I 1, 437 (1972).

The present invention therefore also relates to novel compounds of the formula I in which X, R, Z and n are as defined above, and to salts thereof, with the exception of compounds of the formula I in which X is oxygen, R=—$OCH_3$, —$OC_2H_5$, —O—$CH_2$—CH=CH—$C_6H_5$, —$OCH_2$CH=$CHCH_3$ or —$OCH_2CH_2$CH=$CHCH_3$ and n=0.

The novel compounds of the formula I can be prepared analogously to the processes described in the literature mentioned. For example, compounds of the formula I are obtained by reacting a styrene derivative of the formula II

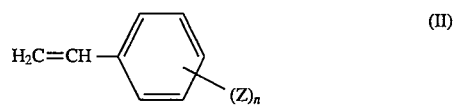

with a compound of the formula III

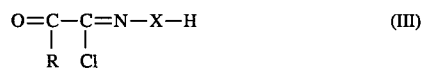

where in formulae II and III R, Z, n and X have the abovementioned meanings. This process is also a subject of the present invention.

The invention is preferably carried out in an aprotic, dipolar organic solvent such as ether at −10° C. up to the boiling point of the reaction mixture and in the presence of an organic base such as triethylamine and pyridine or of an inorganic base such as potassium carbonate, sodium carbonate or sodium hydrogen carbonate.

The compounds of the formulae II and III are known or can be prepared by generally known processes (see, for example, J. Amer. Chem. Soc. 46, 731 (1924); J. Org. Chem. 25, 1160 (1960)).

The compounds of the formula I according to the invention reduce, or prevent, phytotoxic secondary effects of herbicides which can occur when the herbicides are employed in crops, and they can therefore be referred to, in the customary manner, as antidotes or safeners. They can be applied together with herbicidal active substances or in any desired sequence, and are then capable of reducing, or completely abolishing, harmful secondary effects of these herbicides in crop plants, without impairing the activity of these herbicides against weeds.

This allows the field of application of the conventional crop protection agents to be widened quite considerably.

Examples of herbicidal active substances whose phytotoxic secondary effects to crop plants can be reduced by means of the compounds of the formula I are carbamates, thiocarbamates, haloacetanilides, substituted phenoxy-, naphthoxy- and phenoxycarboxylic acid derivatives as well as heteroaryloxyphenoxy-alkanecarboxylic acid derivatives, such as quinolyloxy-, quinoxalyloxy-, pyridyloxy-, benzoxazolyloxy- and benzothiazolyloxy-phenoxyalkanecarboxylic acid esters, cyclohexanedione derivatives, imidazolinones and sulfonylureas. Preferred compounds amongst these are esters and salts of phenoxyphenoxy- and heteroaryloxyphenoxy-carboxylic acid, as well as sulfonylureas and imidazolinones.

Examples of suitable herbicidal active substances which can be combined with the safeners according to the invention are:

A) Herbicides of the type of the $(C_1-C_4)$-alkyl, $(C_2-C_4)$-alkenyl or $(C_3-C_4)$-alkynyl phenoxyphenoxy- and heteroaryloxyphenoxy-carboxylates, such as A1) phenoxy-phenoxy- and benzyloxy-phenoxycarboxylic acid derivatives, such as methyl 2-(4-( 2,4-dichlorophenoxy)phenoxy)propionate (diclofop-methyl), methyl 2-(4-(4-bromo- 2-chlorophenoxy)phenoxy)propionate (see DE-A-2,601,548), methyl 2-(4-(4-bromo-2-fluorophenoxy)phenoxy)propionate (see U.S. Pat. No. 4,808,750), methyl 2-(4-(2-chloro- 4-trifluoromethylphenoxy)phenoxy)propionate (see DE-A-2,433, 067), methyl 2-(4-(2-fluoro- 4-trifluoromethylphenoxy)phenoxy)propionate (see U.S. Pat. No. 4,808,750), methyl 2-(4-( 2,4-dichlorobenzyl)phenoxy)propionate (see DE-A-2,417,487, ethyl 4-(4-( 4-trifluoromethylphenoxy)phenoxy)pent-2-enoate, methyl 2-(4-( 4-trifluoromethylphenoxy)phenoxy)propionate (see DE-A-2,433,067), A2) "mononuclear" heteroaryloxyphenoxyalkanecarboxylic acid derivatives, for example ethyl 2-(4-(3,5-dichloropyridyl- 2-oxy)phenoxy)propionate (see EP-A-2925), propargyl 2-(4-(3,5-dichloropyridyl-2-oxy)phenoxy)propionate (see EP-A-3114), methyl 2-(4-(3-chloro- 5-trifluoromethyl-2-pyridyloxy)phenoxy)propionate (see EP-A-3890), ethyl 2-(4-(3-chloro-5-trifluoromethyl- 2-pyridyloxy)phenoxy)propionate (see EP-A-3890), propargyl 2-(4-(5-chloro-3-fluoro- 2-pyridyloxy)phenoxy)propionate (EP-A-191, 736), butyl 2-(4-(5-trifluoromethyl-2-pyridyloxy)phenoxy)propionate (fluazifop-methyl), A3) "dinuclear" heteroaryloxyphenoxyalkanecarboxylic acid derivatives, for example methyl and ethyl 2-(4-(6-chloro- 2-quinoxalyloxy)phenoxy)propionate (quizalofop-methyl and -ethyl), methyl 2-(4-(6-fluoro-2-quinoxalyloxy)phenoxy)propionate (see J. Pest. Sci. Vol. 10, 61 (1985)), 2-(4-(6-chloro- 2-quinoxalyloxy)phenoxy)propionic acid and its esters such as the 2-isopropylideneaminooxyethyl ester or the tetrahydrofurfuryl ester (propaquizafop and esters), ethyl 2-(4-(6-chlorobenzoxazol- 2-yloxy)phenoxy)propionate (fenoxaprop-ethyl) and ethyl 2-(4-(6-chlorobenzothiazol- 2-yloxy)phenoxypropionate (see DE-A-2,640, 730).

B) Active substances from the sulfonylurea series such as, for example, pyrimidine- or triazinylaminocarbonyl-[benzene-, pyridine-, pyrazole-, thiophene- and (alkylsulfonyl)alkylamino-]sulfamides. Preferred as substituents on the pyrimidine ring or triazine ring are alkoxy, alkyl, haloalkoxy, haloalkyl, halogen or dimethylamino, where all substituents can be combined independently of one another. Preferred substituents in the benzene, pyridine, pyrazole, thiophene or (alkylsulfonyl)alkylamino moiety are alkyl, alkoxy, halogen, nitro, alkoxycarbonyl, aminocarbonyl, alkylaminocarbonyl, dialkylaminocarbonyl, alkoxyaminocarbonyl, alkyl, alkoxyaminocarbonyl, haloalkoxy, haloalkyl, alkylcarbonyl, alkoxyalkyl, (alkanesulfonyl)alkylamino. Examples of suitable sulfonylureas are B1) phenyl- and benzylsulfonylureas and related compounds, for example 1-(2-chlorophenylsulfonyl)-3-(4-methoxy- 6-methyl-1,3,5-triazin-2-yl)-urea (chlorosulfuron), 1-(2-ethoxycarbonylphenylsulfonyl)-3-( 4-chloro-6-methoxypyrimidin-2-yl)-urea (chlorimuron-ethyl), 1-(2-methoxyphenylsulfonyl)-3-( 4-methoxy-6-methyl-1,3,5-triazin-2-yl)-urea (metsulfuron-methyl), 1-(2-chloroethoxy-phenylsulfonyl)-3-( 4-methoxy-6-methyl- 1,3,5-triazin-2-yl)-urea (triasulfuron), 1-(2-methoxycarbonyl-phenylsulfonyl)-3-( 4,6-dimethylpyrimidin-2-yl)-urea (sulfometuron-methyl), 1-(2-methoxycarbonylphenylsulfonyl)-3-( 4-methoxy-6-methyl- 1,3,5-triazin-2-yl)-3-methylurea (tribenuron-methyl) 1-(2-methoxycarbonylbenzylsulfonyl)-3-( 4,6-dimethoxypyrimidin-2-yl)-urea (bensulfuron-methyl) 1-(2-methoxycarbonylphenylsulfonyl)-3-( 4,6-bis-(difluoromethoxy)-pyrimidin- 2-yl)-urea (pirimisulfuron-methyl), 3-(4-ethyl-6-methoxy-1,3,5-triazin- 2-yl)-1-(2,3-dihydro- 1,1-dioxo-2-methylbenzo[b]thiophene-7-sulfonyl)-urea (see EP-A-79,683), 3-(4-ethoxy-6-ethyl-1,3,5-triazin- 2-yl)-1-(2,3-dihydro- 1,1-dioxo-2-methylbenzo[b]thiophene-7-sulfonyl)-urea (see EP-A-79,683), B2) thienylsulfonylureas, for example 1-(2-methoxycarbonylthiophen-3-yl)-3-( 4-methoxy-6-methyl- 1,3,5-triazin-2-yl)-urea (thifensulfuron-methyl), B3) pyrazolylsulfonylureas, for example 1-(4-ethoxycarbonyl-1-methylpyrazol-5-yl-sulfonyl)- 3-(4,6-dimethoxypyrimidin-2-yl)-urea (pyrazosulfuronmethyl), methyl 3-chloro-5-(4,6-dimethoxypyrimidin-2-ylcarbamoylsulfamoyl)-1-methylpyrazol-4-carboxylate (see EP-A-282,613) and methyl 5-(4,6-dimethylpyrimidin- 2-yl-carbamoylsulfamoyl)- 1-(2-pyridyl)-pyrazole-4-carboxylate (NC 330, see Brighton Crop Prot. Conf. Weeds 1991 Vol. 1, p. 45 et seq.).

B4) Sulfonediamide derivatives, for example 3-(4,6-dimethoxypyrimidin-2-yl)- 1-(N-methyl-N-methylsulfonylaminosulfonyl)-urea (amidosulfuron) and structural analogs (see EP-A-0,131,258 and Z. Pfl. Krankh. Pfl. Schutz, Special Edition XII, 489–497 (1990)), B5) pyridylsulfonylureas, for example 1-(3-N,N-dimethylaminocarbonylpyridin- 2-yl-sulfonyl)-3-( 4,6-dimethoxypyrimidin-2-yl)-urea (nicosulfuron), 1-(3-ethylsulfonylpyridin-2-yl-sulfonyl)- 3-(4,6-dimethoxypyrimidin- 2-yl)-urea (DPX-E 9636, see Brighton Crop Prot. Conf.—Weeds—1989, p. 23 et seq.), pyridylsulfonylureas as are described in German Patent Applications P 40 00 503.8 (HOE 90/F 006) and P 40 30 577.5 (HOE 90/F 293), preferably those of the formula IV or salts thereof,

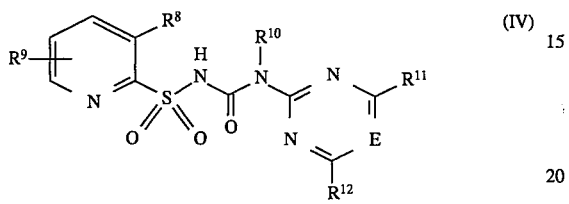

in which

E is CH or N, preferably CH, $R^8$ is iodine or $NR^{13}R^{14}$, $R^9$ is hydrogen, halogen, cyano, $(C_1-C_3)$-alkyl, $(C_1-C_3)$-alkoxy, $(C_1-C_3)$-haloalkyl, $(C_1-C_3)$-haloalkoxy, $(C_1-C_3)$-alkylmercapto, $(C_1-C_3)$-alkoxy-$(C_1-C_3)$-alkyl, $(C_1-C_3)$-alkoxy-carbonyl, mono- or di-$(C_1-C_3)$-alkylamino, $(C_1-C_3)$-alkyl-sulfinyl or -sulfonyl, $SO_2NR^aR^b$ or $CO-NR^aR^b$, in particular hydrogen, $R^a$ and $R^b$ independently of one another are hydrogen, $(C_1-C_3)$-alkyl, $(C_1-C_3)$-alkenyl, $(C_1-C_3)$-alkynyl, or together are $-(CH_2)_4-$, $-(CH_2)_5-$ or $(CH_2)_2-O-(CH_2)_2-$, $R^{10}$ is hydrogen or $CH_3$, $R^{11}$ is halogen, $(C_1-C_2)$-alkyl, $(C_1-C_2)$-alkoxy, $(C_1-C_2)$-haloalkyl, preferably $CF_3$, $(C_1-C_2)$-haloalkoxy, preferably $OCHF_2$ or $OCH_2CF_3$, $R^{12}$ is $(C_1-C_2)$-alkyl, $(C_1-C_2)$-haloalkoxy, preferably $OCHF_2$, or $(C_1-C_2)$-alkoxy, and $R^{13}$ is $(C_1-C_4)$-alkyl and $R^{14}$ is $(C_1-C_4)$-alkylsulfonyl, or $R^{13}$ and $R^{14}$ together are a chain of the formula $-(CH_2)_3SO_2-$ or $-(CH_2)_4 SO_2-$, for example 3-(4, 6-dimethoxypyrimidin- 2-yl)-1-[(3-(N-methylsulfonyl-N-methylamino)-pyridin- 2-yl)-sulfonyl]-urea, B6) alkoxyphenoxysulfonylureas as are described in EP-A-0,342,569, preferably those of the formula V or salts thereof

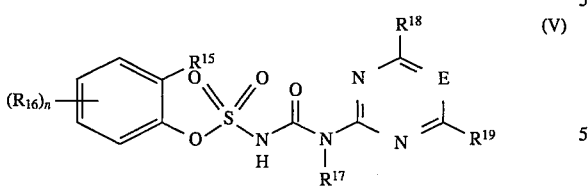

in which

E is CH or N, preferably CH, $R^{15}$ is ethoxy, propoxy or isopropoxy, $R^{16}$ is hydrogen, halogen, nitro, $CF_3$, CN, $(C_1-C_4)$-alkyl, $(C_1-C_4)$-alkoxy, $(C_1-C_4)$-alkylmercapto or $(C_1-C_3)$-alkoxy-carbonyl, preferably in the 6-position on the phenyl ring, n is 1, 2 or 3, preferably 1, $R^{17}$ is hydrogen, $(C_1-C_4)$-alkyl or $(C_3-C_4)$-alkenyl, $R^{18}$ and $R^{19}$ independently of one another are halogen, $(C_1-C_2)$-alkyl, $(C_1-C_2)$-alkoxy, $(C_1-C_2)$-haloalkyl, $C_1-C_2$-haloalkoxy or $(C_1-C_2)$-alkoxy-$(C_1-C_2)$-alkyl, preferably $OCH_3$ or $CH_3$, for example 3-(4,6-dimethoxypyrimidin-2-yl)- 1-(2-ethoxyphenoxy)-sulfonylurea, and other related sulfonylurea derivatives and mixtures of these.

C) Chloroacetanilide herbicides such as N-methoxymethyl-2,6-diethylchloroacetanilide (alachlor), N-(3'-methoxyprop-2'-yl)-2-methyl- 6-ethylchloroacetanilide (metolachlor), N-(3-methyl-1,2,4-oxadiazol-5-ylmethyl)- 2,6-dimethylchloroacetanilide, N-(2,6-dimethylphenyl)-N-(1-pyrazolylmethyl)-chloroacetamide (metazachlor), D) thiocarbamates such as S-ethyl N,N-dipropylthiocarbamate (EPTC) or S-ethyl N,N-diisobutylthiocarbamate (burylate)

E) cyclohexanedione derivatives such as methyl 3-(1-allyloxyimino)butyl)-4-hydroxy- 6,6-dimethyl- 2-oxocyclohex-3-enecarboxylate (alloxydim) 2-(N-ethoxybutyrimidoyl)-5-(2-ethylmercaptopropyl)-3-hydroxy-2-cyclohexen-1-one (sethoxydim), 2-(N-ethoxybutyrimidoyl)-5-(2-phenylmercaptopropyl)-3-hydroxy-2-cyclohexen-1-one (cloproxydim), 2-(1-(3-chloroallyloxy)iminobutyl)-5-( 2-ethylmercapto)-propyl)- 3-hydroxy-2-cyclohexen-1-one 2-(1-(3-chloroallyloxy)iminopropyl)-5-(2-ethylmercapto)-propyl)-3-hydroxycyclohex-2-en-1-one (clethodim), 2-(1-allyloxyiminobutyl)-4-methoxycarbonyl- 5,5-dimethyl-3-oxocyclohexenol, 2-(1-(ethoxyimino)butyl)-3-hydroxy- 5-(thian-3-yl)cyclo-hex-2-enone (cycloxydim), or 2-(1-ethoxyiminopropyl)-5-(2,4,6-trimethylphenyl)-3-hydroxy-2-cyclohexen- 1-one (tralkoxydim).

F) Imidazolinones such as 2-carboxyphenyl- or 2-carboxyheteroarylimidazolinones, their salts and their esters (for example alkyl esters), for example the mixture of methyl 2-(4-isopropyl-4-methyl-5-oxo- 2-imidazolin-2-yl)- 5-methylbenzoate and 2-(4-isopropyl-4-methyl-5-oxo- 2-imidazolin-2-yl)-4methylbenzoic acid (imazamethabenz), and 5-ethyl-2-(4-isopropyl-4-methyl-5-oxo-2-imidazolin-2-yl)-pyridin-3-carboxylic acid and the esters and salts thereof, for example the $NH_4$ salt (imazethapyr), 2-[4,5-dihydro-4-methyl-4-(1-methylethyl)-5-oxo-1H-imidazol-2-yl]-5-methyl-3-pyridinecarboxylic acid and the esters and salts thereof (imazethamethapyr) and 2-(4-isopropyl-4-methyl-5-oxo- 2-imidazolin-2-yl)-quinoline-3-carboxylic acid and the esters and salts thereof, for example the $NH_4$ salt (imazaquin).

The abovementioned herbicidal active substances from groups A to F are known to those skilled in the art and are generally described in "The Pesticide Manual", British Crop Protection Council, 9th Edition (1990–91) or in "Agricultural Chemicals Book II-Herbicides-", by W. T. Thompson, Thompson Publications, Fresno Calif., USA 1990 or in "Farm Chemicals Handbook '90", Meister Publishing Company, Willoughby Ohio, USA 1990.

The herbicidal active substances and the safeners mentioned can be applied together (in the form of a finished formulation or by the tank mix method) or one after the other, in any desired sequence. The ratio by weight of safener:herbicide can vary within wide limits and is preferably in the range from 1:10 to 10:1, in particular 1:10 to 5:1. The amounts of herbicides and safener which are ideal in each case depend on the type of herbicide used or on the safener used as well as on the nature of the plant stock to be treated, and they can be determined for each individual case by appropriate preliminary experiments.

The safeners are mainly employed in particular in cereal crops (wheat, rye, barley, oats), rice, maize, sorghum, but also cotton and soybean, preferably cereals and maize.

A particular advantage of the safeners of the formula I according to the invention can found when they are combined with active substances from the group of the sulfonylureas and/or imidazolinones. Herbicides of the abovementioned structural classes are primary inhibitors of the key enzyme acetolactate synthase (ALS) in the plants and are at least partially related as regards the mechanism of action. Some herbicides of these structure classes have no, or not sufficient, selectivity when used in particular in cereal crops and/or maize. A combination with the safeners according to the invention allows outstanding selectivities to be achieved with these herbicides, even in cereals or maize.

Depending on their properties, the safeners of the formula I can be used for pretreating the seed of the crop plant (seed treatment), or they can be incorporated into the seed furrows prior to sowing, or used together with the herbicide prior to, or after, plant emergence. Pre-emergence treatment includes both the treatment of the area under cultivation prior to sowing and the treatment of the area under cultivation where seed has been sown but growth of the crop plants has not yet taken place. Application together with the herbicide is preferred. Tank mixes or ready mixes can be employed for this purpose. Depending on the indication and the herbicide used, the safener dosage rates required can vary within wide limits and are generally in a range from 0.001 to 5 kg, preferably 0.005 to 0.5 kg, of active substance per hectare.

The present invention therefore also relates to a method of protecting crop plants against phytotoxic secondary effects of herbicides, which comprises applying an effective amount of a compound of the formula I to the plants, parts of plants, seeds of plants or the area under cultivation, either before, after or simultaneously with, the herbicide.

The invention also relates to crop-protecting compositions which contain an active substance of the formula I and customary formulation auxiliaries, as well as herbicidal compositions which contain an active substance of the formula I and a herbicidal active substance, and formulation auxiliaries conventionally used for crop protection purposes.

The compounds of the formula I or their combinations with one or more of the herbicidal active substances mentioned can be formulated i.e. brought to a use form suitable for crop protection, in a variety of ways, as predetermined by the biological and/or physicochemical parameters. The following possibilities are therefore suitable for formulation: wettable powders (WP), emulsifiable concentrates (EC), water-soluble powders (SP), water-soluble concentrates (SL), concentrated emulsions (EW) such as oil-in-water and water-in-oil emulsions, sprayable solutions or emulsions, capsule suspensions (CS), dispersions on an oil or water base (SC), suspoemulsions, suspension concentrates, dusts (DP), oil-miscible solutions (OL), seed-dressing agents, granules (GR) in the form of microgranules, spray granules, coated granules and adsorption granules, granules for soil application or scattering, water-dispersible granules (WSG), ULV formulations, microcapsules or waxes.

These abovementioned formulation types and processes for their preparation are known in principle and are described, for example, in: Winnacker-Küchler, "Chemische Technologie [Chemical Technology]", Volume 7, C. Hauser Verlag Munich, 4th Ed., 1986; Wade van Valkenberg, "Pesticide Formulations", Marcel Dekker N.Y., 73; K. Martens, "Spray Drying Handbook", 3rd Ed. 1979, G. Goodwin Ltd. London.

The formulation auxiliaries required, such as inert materials, surfactants, solvents and other additives, are likewise known and are described, for example, in: Watkins, "Handbook of Insecticide Dust Diluents and Carriers", 2nd Ed., Darland Books, Caldwell N.J.; H.v.Olphen, "Introduction to Clay Colloid Chemistry", 2nd Ed., J. Wiley & Sons, N.Y.; Marsden, "Solvents Guide", 2nd Ed., Interscience, N.Y. 1963; McCutcheon's, "Detergents and Emulsifiers Annual", MC Publ. Corp. Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active Ethylene Oxide Adducts]", Wiss. Verlagsgesell., Stuttgart 1976; Winnacker-Küchler, "Chemische Technologie [Chemical Technology]", Volume 7, C. Hauser Verlag Munich, 4th Ed. 1986.

Combinations with other pesticidally active substances, fertilizers and/or growth regulators may also be prepared on the basis of these formulations, for example in the form of a readymix or as a tank mix.

Wettable powders are preparations which are uniformly dispersible in water and which, besides the active substance, also contain surfactants of ionic and/or nonionic character (wetting agents, dispersing agnets), for example polyoxethylated alkylphenols, polyoxethylated fatty alcohols and fatty amines, fatty alcohol polyglycol ether sulfates, alkanesulfonates or alkylarylsulfonates, and dispersing agents, for example sodium ligninsulfonate, sodium 2,2'-dinaphthylmethane-6,6'-disulfonate, sodium dibutylnaphthalenesulfonate, or alternatively sodium oleoylmethyltaurinate, in addition to a diluent or inert substance.

Emulsifiable concentrates are prepared by dissolving the active substance in an organic solvent, for example butanol, cyclohexanone, dimethylformamide, xylene and also higher-boiling aromatic compounds or hydrocarbons, with the addition of one or more surfactants of ionic and/or non-ionic character (emulsifiers). Examples of emulsifiers which can be used are: calcium salts of an alkylarylsulfonic acid, such as calcium dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products (for example block copolymers), alkyl polyethers or polyoxyethylene sorbitan esters, such as sorbitan fatty acid esters, for example polyoxyethylene sorbitan fatty acid esters.

Dusts can be obtained by grinding the active substance with finely divided solid substances, for example talc or natural clays, such as kaolin, bentonite and pyrophyllite or diatomaceous earth.

Granules can be produced either by spraying the active substance onto adsorptive,,granulated inert material or by applying active substance concentrates onto the surface of carriers, such as sand, kaolinites or granulated inert material, by means of binders, for example polyvinyl alcohol, sodium polyacrylate or, alternatively, mineral oils. Suitable active substances can also be granulated in the manner which is conventional for the production of fertilizer granules, if desired in a mixture with fertilizers.

Water-dispersible granules are prepared for example, by customary methods such as spray drying, fluidized-bed granulation, plate granulation, mixing by means of high-speed stirrers, and extrusion methods without solid inert materal.

In general, the agrochemical preparations contain 0.1 to 99% by weight, in particular 0.1 to 95% by weight, of active substances of the formula I (antidote) or of the antidote/ herbicide active substance mixture, and 1 to 99.9% by weight, in particular 5 to 99.8% by weight, of a solid or liquid additive, and 0 to 25% by weight, in particlar 0.1 to 25% by weight, of a surfactant.

The concentration of active substance in wettable powders is, for example, about 10 to 90% by weight; the remainder to 100% by weight is composed of conventional formulation components. In the case of emulsifiable concentrates, the concentration of active substance is about 1 to 80% by weight. Formulations in the form of dusts usually contain 1 to 20% by weight of active substance, sprayable solutions about 0.2 to 20% by weight of active substance. In the case of granules such as water-dispersible granules, the active substance content depends partly on whether the active compound is liquid or solid. Water-dispersible granules generally have a content of between 10 and 90% by weight.

In addition, the active substance formulations mentioned contain, if appropriate, the adhesives, wetting agents, dispersing agents, emulsifiers, penetrants, preservatives, antifreeze agents and solvents, fillers, colorants and carriers, defoamers, evaporation inhibitors, pH regulators and viscosity regulators which are conventional in each case.

For use, the concentrates, present in commercially available form, are diluted, if appropriate, in a customary manner, for example using water in the case of wettable powders, emulsifiable concentrates, dispersions and water-dispersible granules. Preparations in the form of dusts, granules and also sprayable solutions are usually not further diluted with other inert substances before use. The application rate required for the "antidotes" varies with the external conditions, such as, inter alia, temperature, humidity, and the nature of the herbicide used.

The examples which follow serve to illustrate the invention without imposing any restriction:

A. Formulation Examples a) A dust is obtained by mixing 10 parts by weight of a compound of the formula I or an active substance mixture of a herbicide and a compound of the formula I and 90 parts by weight of talc as the inert substance and comminuting the mixture in a hammer mill.

b) A wettable powder which is readily dispersible in water is obtained by mixing 25 parts by weight of a compound of the formula I or an active substance mixture of a herbicide and a safener of the formula I, 64 parts by weight of kaolin-containing quartz as the inert substance, 10 parts by weight of potassium ligninsulfonate and 1 part by weight of sodium oleoylmethyltaurinate as the wetting and dispersing agent, and grinding the mixture in a pinned disk-mill.

c) A dispersion concentrate which is readily dispersible in water is obtained by mixing 20 parts by weight of a compound of the formula I or an active substance mixture of a herbicide and a safener of the formula I, 6 parts by weight of alkylphenol polyglycol ether (ᴿTriton X 207), 3 parts by weight of isotridecanol polyglycol ether (8 EO) and 71 parts by weight of paraffinic mineral oil (boiling range, for example, about 255° to above 277° C.), and grinding the mixture in a ball mill to a fineness of below 5 microns.

d) An emulsifiable concentrate is obtained from 15 parts by weight of a compound of the formula I or an active substance mixture of a herbicide and a safener of the formula I, 75 parts by weight of cyclohexanone as the solvent and 10 parts by weight of oxethylated nonylphenol as the emulsifier.

e) Water-dispersible granules are obtained by mixing 75 parts by weight of a compound of the formula I or an active substance mixture of a herbicide and a safener of the formula I, 10 parts by weight of calcium ligninsulfonate,
5 parts by weight of sodium lauryl sulfate,
3 parts by weight of polyvinyl alcohol and
7 parts by weight of kaolin, grinding the mixture on a pinned disk mill, and granulating the powder in a fluidized bed by spraying on water as the granulation liquid.

f) Alternatively, water-dispersible granules are obtained by homogenizing and precomminuting 25 parts by weight of a compound of the formula I or of an active substance mixture of a herbicide and a safener of the formula I, 5 parts by weight of sodium 2,2'-dinaphthyl-methane-6,6'-disulfonate,
2 parts by weight of sodium oleoylmethyltaurinate,
1 parts by weight of polyvinyl alcohol,
17 parts by weight of calcium carbonate and
50 parts by weight of water in a colloid mill, subsequently grinding the mixture in a bead mill, and atomizing and drying the resulting suspension in a spray tower using a single-substance nozzle.

B. Chemical Examples

Ethyl 5-(2-methoxyphenyl)-2-isoxazoline- 3-carboxylate (Example 125, see Table 1)

4.2 g of 2,4-difluorostyrene and 4.55 g of ethyl 2-chloro-2-hydroximinoacetate are introduced into 350 ml of ether, and the mixture is cooled to 0° C. 3.03 g of triethylamine are added dropwise to this mixture at 0° C. The mixture is stirred for 3 hours at room temperature, 50 ml of water are then added, and the mixture is extracted using ether. After drying over $MgSO_4$, the ether is distilled off, and the residue is purified over a silica column (eluent: n-heptane:ethyl acetate=8:2). This gave 6.68 g ( 86% of theory) of product of refractive index $[n]_D^{20}=1.5019$.

The derivatives of Table 1 below are obtained analogously.

TABLE 1

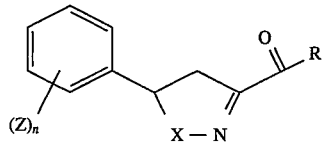

| Example No. | $(Z)_n$ | R | X | Melting point/$[n]_D^{20}$ |
|---|---|---|---|---|
| 1 | n = 0 | OH | O | |
| 2 | n = 0 | $OCH_3$ | O | 40° C. |
| 3 | n = 0 | $OC_2H_5$ | O | 1.5331 |
| 4 | n = 0 | $n\text{-}OC_3H_7$ | O | |
| 5 | n = 0 | $i\text{-}OC_3H_7$ | O | |
| 6 | n = 0 | $n\text{-}OC_4H_9$ | O | |
| 7 | n = 0 | $OCH_2CO_2C_2H_5$ | O | |
| 8 | n = 0 | $OC_6H_5$ | O | |
| 9 | n = 0 | $OCH_2C_6H_5$ | O | |
| 10 | n = 0 | $OCH_2CH=CH_2$ | O | |
| 11 | n = 0 | $OCH_2C\equiv CH$ | O | |
| 12 | n = 0 | $OCH_2Si(CH_3)_3$ | O | |
| 13 | n = 0 | $O^-K^+$ | O | |
| 14 | 2-Cl | OH | O | |
| 15 | 2-Cl | $OCH_3$ | O | |
| 16 | 2-Cl | $OC_2H_5$ | O | |

TABLE 1-continued

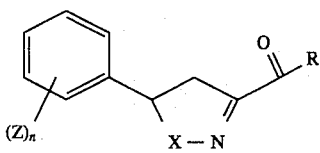

| Example No. | $(Z)_n$ | R | X | Melting point/$[n]_D^{20}$ |
|---|---|---|---|---|
| 17 | 2-Cl | n-OC$_3$H$_7$ | O | |
| 18 | 2-Cl | i-OC$_3$H$_7$ | O | |
| 19 | 2-Cl | n-OC$_4$H$_9$ | O | |
| 20 | 2-Cl | OCH$_2$CO$_2$C$_2$H$_5$ | O | |
| 21 | 2-Cl | OC$_6$H$_5$ | O | |
| 22 | 2-Cl | OCH$_2$C$_6$H$_5$ | O | |
| 23 | 2-Cl | OCH$_2$CH=CH$_2$ | O | |
| 24 | 2-Cl | OCH$_2$C≡CH | O | |
| 25 | 2-Cl | OCH$_2$Si(CH$_3$)$_3$ | O | |
| 26 | 2-Cl | O$^-$K$^+$ | O | |
| 27 | 4-Cl | OH | O | |
| 28 | 4-Cl | OCH$_3$ | O | 78° C. |
| 29 | 4-Cl | OC$_2$H$_5$ | O | 58° C. |
| 30 | 4-Cl | n-OC$_3$H$_7$ | O | |
| 31 | 4-Cl | i-OC$_3$H$_7$ | O | |
| 32 | 4-Cl | n-OC$_4$H$_9$ | O | |
| 33 | 4-Cl | OCH$_2$CO$_2$C$_2$H$_5$ | O | |
| 34 | 4-Cl | OC$_6$H$_5$ | O | |
| 35 | 4-Cl | OCH$_2$C$_6$H$_5$ | O | |
| 36 | 4-Cl | OCH$_2$CH=CH$_2$ | O | |
| 37 | 4-Cl | OCH$_2$C≡CH | O | |
| 38 | 4-Cl | OCH$_2$Si(CH$_3$)$_3$ | O | |
| 39 | 2,4-Cl$_2$ | OH | O | |
| 40 | 2,4-Cl$_2$ | OCH$_3$ | O | 83–84° C. |
| 41 | 2,4-Cl$_2$ | OC$_2$H$_5$ | O | 75–76° C. |
| 42 | 2,4-Cl$_2$ | n-OC$_3$H$_7$ | O | |
| 43 | 2,4-Cl$_2$ | i-OC$_3$H$_7$ | O | |
| 44 | 2,4-Cl$_2$ | n-OC$_4$H$_9$ | O | |
| 45 | 2,4-Cl$_2$ | OCH$_2$CO$_2$C$_2$H$_5$ | O | |
| 46 | 2,4-Cl$_2$ | OC$_6$H$_5$ | O | |
| 47 | 2,4-Cl$_2$ | OCH$_2$C$_6$H$_5$ | O | |
| 48 | 2,4-Cl$_2$ | OCH$_2$CH=CH$_2$ | O | |
| 49 | 2,4-Cl$_2$ | OCH$_2$C≡CH | O | |
| 50 | 2,4-Cl$_2$ | OCH$_2$Si(CH$_3$)$_3$ | O | |
| 51 | 2,4-Cl$_2$ | OCH$_2$CO$_2$CH$_3$ | O | |
| 52 | 2,6-Cl$_2$ | OH | O | |
| 53 | 2,6-Cl$_2$ | OCH$_3$ | O | 116–117° C. |
| 54 | 2,6-Cl$_2$ | OC$_2$H$_5$ | O | 105–106° C. |
| 55 | 2,6-Cl$_2$ | n-OC$_3$H$_7$ | O | |
| 56 | 2,6-Cl$_2$ | i-OC$_3$H$_7$ | O | |
| 57 | 2,6-Cl$_2$ | n-OC$_4$H$_9$ | O | |
| 58 | 2,6-Cl$_2$ | OCH$_2$CO$_2$C$_2$H$_5$ | O | |
| 59 | 2,6-Cl$_2$ | OC$_6$H$_5$ | O | |
| 60 | 2,6-Cl$_2$ | OCH$_2$C$_6$H$_5$ | O | |
| 61 | 2,6-Cl$_2$ | OCH$_2$CH=CH$_2$ | O | |
| 62 | 2,6-Cl$_2$ | OCH$_2$C≡CH | O | |
| 63 | 2,6-Cl$_2$ | OCH$_2$Si(CH$_3$)$_3$ | O | |
| 64 | 4-OCH$_3$ | OH | O | |
| 65 | 4-OCH$_3$ | OCH$_3$ | O | 71° C. |
| 66 | 4-OCH$_3$ | OC$_2$H$_5$ | O | 1.5402 |
| 67 | 4-OCH$_3$ | n-OC$_3$H$_7$ | O | |
| 68 | 4-OCH$_3$ | i-OC$_3$H$_7$ | O | |
| 69 | 4-OCH$_3$ | n-OC$_4$H$_9$ | O | |
| 70 | 4-OCH$_3$ | OCH$_2$CO$_2$C$_2$H$_5$ | O | |
| 71 | 4-OCH$_3$ | OC$_6$H$_5$ | O | |
| 72 | 4-OCH$_3$ | OCH$_2$C$_6$H$_5$ | O | |
| 73 | 4-OCH$_3$ | OCH$_2$CH=CH$_2$ | O | |
| 74 | 4-OCH$_3$ | OCH$_2$C≡CH | O | |
| 75 | 4-OCH$_3$ | OCH$_2$Si(CH$_3$)$_3$ | O | |
| 76 | 2-OCH$_3$ | OH | O | |
| 77 | 2-OCH$_3$ | OCH$_3$ | O | |
| 78 | 2-OCH$_3$ | OC$_2$H$_5$ | O | |
| 79 | 2-OCH$_3$ | n-OC$_3$H$_7$ | O | |

TABLE 1-continued

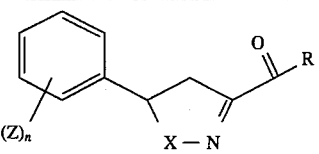

| Example No. | $(Z)_n$ | R | X | Melting point/$[n]_D^{20}$ |
|---|---|---|---|---|
| 80 | 2-OCH$_3$ | i-OC$_3$H$_7$ | O | |
| 81 | 2-OCH$_3$ | n-OC$_4$H$_9$ | O | |
| 82 | 2-OCH$_3$ | OCH$_2$CO$_2$C$_2$H$_5$ | O | |
| 83 | 2-OCH$_3$ | OC$_6$H$_5$ | O | |
| 84 | 2-OCH$_3$ | OCH$_2$C$_6$H$_5$ | O | |
| 85 | 2-OCH$_3$ | OCH$_2$CH=CH$_2$ | O | |
| 86 | 2-OCH$_3$ | OCH$_2$C≡CH | O | |
| 87 | 2-OCH$_3$ | OCH$_2$Si(CH$_3$)$_3$ | O | |
| 88 | 2-CH$_3$ | OH | O | |
| 89 | 2-CH$_3$ | OCH$_3$ | O | |
| 90 | 2-CH$_3$ | OC$_2$H$_5$ | O | |
| 91 | 2-CH$_3$ | n-OC$_3$H$_7$ | O | |
| 92 | 2-CH$_3$ | i-OC$_3$H$_7$ | O | |
| 93 | 2-CH$_3$ | n-OC$_4$H$_9$ | O | |
| 94 | 2-CH$_3$ | OCH$_2$CO$_2$C$_2$H$_5$ | O | |
| 95 | 2-CH$_3$ | OC$_6$H$_5$ | O | |
| 96 | 2-CH$_3$ | OCH$_2$C$_6$H$_5$ | O | |
| 97 | 2-CH$_3$ | OCH$_2$CH=CH$_2$ | O | |
| 98 | 2-CH$_3$ | OCH$_2$C≡CH | O | |
| 99 | 2-CH$_3$ | OCH$_2$Si(CH$_3$)$_3$ | O | |
| 100 | 2-CH$_3$ | OCH$_3$ | S | |
| 101 | 2-CH$_3$ | OC$_2$H$_5$ | S | |
| 102 | 4-Cl | OCH$_3$ | S | |
| 103 | 4-Cl | OC$_2$H$_5$ | S | |
| 104 | 2,4-Cl$_2$ | OCH$_3$ | S | |
| 105 | 2,4-Cl$_2$ | OC$_2$H$_5$ | S | |
| 106 | 2,6-Cl$_2$ | OCH$_3$ | S | |
| 107 | 2,6-Cl$_2$ | OC$_2$H$_5$ | S | |
| 108 | 4-OCH$_3$ | OCH$_3$ | S | |
| 109 | 4-OCH$_3$ | OC$_2$H$_5$ | S | |
| 110 | 2-OCH$_3$ | OCH$_3$ | S | |
| 111 | 2-OCH$_3$ | OC$_2$H$_5$ | S | |
| 112 | 2-CH$_3$ | OCH$_3$ | S | |
| 113 | 2-CH$_3$ | OC$_2$H$_5$ | S | |
| 114 | 2-Cl | N(CH$_3$)$_2$ | O | |
| 115 | 2-Cl | NHNH$_2$ | O | |
| 116 | 2-Cl | NH$_2$ | O | |
| 117 | 2,4-Cl$_2$ | N(CH$_3$)$_2$ | O | |
| 118 | 2,4-Cl$_2$ | NHNH$_2$ | O | |
| 119 | 2,4-Cl$_2$ | NH$_2$ | O | |
| 120 | 4-Cl | N(CH$_3$)$_2$ | O | |
| 121 | 4-Cl | NHNH$_2$ | O | |
| 122 | 4-Cl | NH$_2$ | O | |
| 123 | 2,4-F$_2$ | OH | O | 142° C. (decomp.) |
| 124 | 2,4-F$_2$ | OCH$_3$ | O | 1.5101 |
| 125 | 2,4-F$_2$ | OC$_2$H$_5$ | O | 1.5019 |
| 126 | 2,4-F$_2$ | n-OC$_3$H$_7$ | O | |
| 127 | 2,4-F$_2$ | i-OC$_3$H$_7$ | O | |
| 128 | 2,4-F$_2$ | n-OC$_4$H$_9$ | O | |
| 129 | 2,4-F$_2$ | OCH$_2$CO$_2$C$_2$H$_5$ | O | |
| 130 | 2,4-F$_2$ | OC$_6$H$_5$ | O | |
| 131 | 2,4-F$_2$ | OCH$_2$C$_6$H$_5$ | O | |
| 132 | 2,4-F$_2$ | OCH$_2$CH=CH$_2$ | O | |
| 133 | 2,4-F$_2$ | OCH$_2$C≡CH | O | |
| 134 | 2,4-F$_2$ | −O$^-$K$^+$ | O | |
| 135 | 2,4-F$_2$ | −O$^-$Na$^+$ | O | |
| 136 | 3-Cl | OH | O | |
| 137 | 3-Cl | OCH$_3$ | O | 53° C. |
| 138 | 3-Cl | OC$_2$H$_5$ | O | 1.5305 |
| 139 | 3-Cl | n-OC$_3$H$_7$ | O | |
| 140 | 3-Cl | i-OC$_3$H$_7$ | O | |
| 141 | 3-Cl | n-OC$_4$H$_9$ | O | |
| 142 | 3-Cl | OCH$_2$CO$_2$C$_2$H$_5$ | O | |
| 143 | 3-Cl | OC$_6$H$_5$ | O | |
| 144 | 3-Cl | OCH$_2$C$_6$H$_5$ | O | |

TABLE 1-continued

[Structure: benzene ring with (Z)n substituent, connected to CH-CH2-C(=O)R with X-N group]

| Example No. | (Z)$_n$ | R | X | Melting point/$[n]_D^{20}$ |
|---|---|---|---|---|
| 145 | 3-Cl | OCH$_2$CH=CH$_2$ | O | |
| 146 | 3-Cl | OCH$_2$C≡CH | O | |
| 147 | 3-Cl | —O$^-$K$^+$ | O | |
| 148 | 3-Cl | —O$^-$Na$^+$ | O | |
| 149 | 4-CH$_3$ | OH | O | |
| 150 | 4-CH$_3$ | OCH$_3$ | O | 1.5370 |
| 151 | 4-CH$_3$ | OC$_2$H$_5$ | O | 52° C. |
| 152 | 4-CH$_3$ | n-OC$_3$H$_7$ | O | |
| 153 | 4-CH$_3$ | i-OC$_3$H$_7$ | O | |
| 154 | 4-CH$_3$ | n-OC$_4$H$_9$ | O | |
| 155 | 4-CH$_3$ | OCH$_2$CO$_2$C$_2$H$_5$ | O | |
| 156 | 4-CH$_3$ | OC$_6$H$_5$ | O | |
| 157 | 4-CH$_3$ | OCH$_2$C$_6$H$_5$ | O | |
| 158 | 4-CH$_3$ | OCH$_2$CH=CH$_2$ | O | |
| 159 | 4-CH$_3$ | OCH$_2$C≡CH | O | |
| 160 | 4-CH$_3$ | —O$^-$K$^+$ | O | |
| 161 | 4-CH$_3$ | —O$^-$Na$^+$ | O | |
| 162 | 2,6-(OCH$_3$)$_2$ | OH | O | |
| 163 | 2,6-(OCH$_3$)$_2$ | OCH$_3$ | O | 1.5529 |
| 164 | 2,6-(OCH$_3$)$_2$ | OC$_2$H$_5$ | O | 1.5438 |
| 165 | 2,6-(OCH$_3$)$_2$ | n-OC$_3$H$_7$ | O | |
| 166 | 2,6-(OCH$_3$)$_2$ | i-OC$_3$H$_7$ | O | |
| 167 | 2,6-(OCH$_3$)$_2$ | n-OC$_4$H$_9$ | O | |
| 168 | 2,6-(OCH$_3$)$_2$ | OCH$_2$CO$_2$C$_2$H$_5$ | O | |
| 169 | 2,6-(OCH$_3$)$_2$ | OC$_6$H$_5$ | O | |
| 170 | 2,6-(OCH$_3$)$_2$ | OCH$_2$C$_6$H$_5$ | O | |
| 171 | 2,6-(OCH$_3$)$_2$ | OCH$_2$CH=CH$_2$ | O | |
| 172 | 2,6-(OCH$_3$)$_2$ | OCH$_2$C≡CH | O | |
| 173 | 2,6-(OCH$_3$)$_2$ | —O$^-$K$^+$ | O | |
| 174 | 2,6-(OCH$_3$)$_2$ | —O$^-$Na$^+$ | O | |

C. Biological Examples

Example 1

Wheat and barley were grown in plastic pots in the greenhouse until they had reached the 3-4-leaf stage and then treated in succession with the compounds according to the invention and the herbicidal active substances tested, using the post-emergence method. The herbicidal active substances and the compounds of the formula I were applied in the form of aqueous suspensions or emulsions at a water application rate of 300 to 600 1/ha (converted). 3–4 weeks after the treatment, the plants were scored visually for any type of damage by the herbicides which have been applied, with particular emphasis on the extent of sustained growth inhibition. The assessment was in percentages compared with untreated controls.

The results of Table 2 demonstrate that the compounds according to the invention are capable of effectively reducing severe herbicide damage to crop plants.

Severe damage to the crop plants is markedly reduced even when the herbicide is greatly overdosed, and slight damage is prevented completely. Mixtures of herbicides and compounds according to the invention are therefore outstandingly suitable for selective weed control in cereal crops.

TABLE 2

Safener action of the compounds according to the invention

| Example | No. | kg of a.i./ha | TRAE | HOVU |
|---|---|---|---|---|
| H | | 2.0 | 80 | — |
| | | 0.2 | — | 85 |
| H+ | 124 | 2.0 + 1.25 | 20 | — |
| H+ | 124 | 0.2 + 1.25 | — | 30 |
| H+ | 137 | 2.0 + 1.25 | 25 | — |
| H+ | 137 | 0.2 + 1.25 | — | 35 |

Abbreviations:
TRAE = Triticum aestivum
HOVU = Hordeum vulgare
a.i. = active ingredient
No. = compound of Table 1 with the same number
H = ethyl 2-(4-(6-chlorobenzoxazol-2-yloxy)phenoxy-propionate (fenoxaprop-ethyl)

In the columns under TRAE and HOVU, the adverse effects (herbicidal action) are indicated as percentages (100= plant dies, 0=no damage).

Comparably good results with regard to the crop-plant-protecting action are achieved, for example, by a post-emergence treatment with the compounds of Examples 2, 3, 28, 29, 41, 125 and 138 from Table 1 in cereals at an application rate of between 0.01 and 1.5 kg of active safener substance per ha.

Example 2

Maize plants, dicotyledon weeds and grass weeds are grown in plastic pots in the open or in the greenhouse until they have reached the 4- to 5-leaf stage and treated in succession with herbicides and compounds of the formula I according to the invention by the post-emergence method. The active substances are applied in the form of aqueous suspensions or emulsions at a water application rate of 300 to 600 1/ha (converted). 4 weeks after the treatment, the plants are scored visually for any type of damage by the herbicides which have been applied, with particular emphasis on the extent of sustained growth inhibition. The assessment is in percentages compared with untreated controls.

The results demonstrate that the compounds of the formula I which are used according to the invention are capable of effectively reducing severe herbicide damage on the maize plants. Severe damage to the crop plants is markedly reduced even when the herbicides are greatly overdosed, and slight damage is prevented completely. For example, good safener effects in maize are achieved with 0.01 to 1.5 kg of active substance of the compounds of Examples 2, 3, 28, 29, 41, 124, 125, 137 or 138 from Table 1 per hectare when combined with the herbicide 1-[3-(N,N-dimethylaminocarbonyl)-pyridin-2-ylsulfonyl]- 3-( 4,6-dimethoxypyrimidin-2-yl)-urea (nicosulfuron), 3-(4,6-dimethoxypyrimidin-2-yl)-1-[3-(N-methyl-N-methylsulfonyl-amino)-2-pyridyl-sulfonyl]-urea, 1-(3-ethylsulfonylpyridin-2-ylsulfonyl)-3-(4,6-dimethoxypyrimidin-2-yl)urea (DPX-E 9636), ammonium 5-ethyl-2-(4-isopropyl-4-methyl-5-oxo-2-imidazolin- 2-yl)-pyridine-3-carboxylate (imazethapyram-monium) or 1-(2-methoxycarbonylphenylsulfonyl)-3-(4,6-bis-(difluoromethoxy)-pyrimidin-2-yl)-urea (pirimisulfuron-methyl).

Mixtures of herbicides and compounds of the formula I are therefore outstandingly suitable for selective weed control in maize.

We claim:

1. A crop-plant-protecting compositions which contains at least one compound of the formula I or a salt thereof,

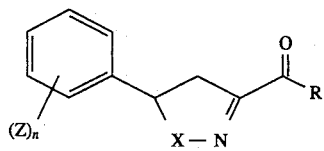

in which

X is an oxygen or sulfur atom,

R is $C_1$–$C_4$-alkoxy, $C_2$–$C_4$-alkenyloxy or hydroxyl,

Z is halogen or $C_1$–$C_4$-alkyl and n is an integer of from 0 to 5 and at least one herbicide selected from the group consisting of phenoxyphenoxy- and heteroaryloxyphenoxy-alkanecarboxylic acid derivatives and sulfonylureas.

2. A composition as claimed in claim 1, wherein

R is $C_1$–$C_4$-alkoxy or hydroxyl,

Z is halogen or methyl and n is an integer of from 0 to 5, and at least one herbicide selected from the group consisting of fenoxaprop-ethyl, fenoxaprop-P-ethyl and a sulfonylurea herbicide selected from pyridinylsulfonylurea herbicides.

3. A composition as claimed in claim 1, wherein

X is an oxygen atom,

R is $C_1$–$C_4$-alkoxy or hydroxyl,

Z is halogen or methyl and n is an integer of from 0 to 2.

4. A composition as claimed in claim 2, wherein

X is an oxygen atom,

R is $C_1$–$C_4$-alkoxy or hydroxyl,

Z is halogen or methyl and n is an integer of from 0 to 2.

5. A composition as claimed in claim 4, containing at least one herbicide selected from the group consisting of fenoxaprop-ethyl and fenoxaprop-P-ethyl.

6. A composition as claimed in claim 4, containing at least one herbicide selected from pyridinylsulfonylurea herbicides.

7. A composition as claimed in claim 5, containing at least the herbicide 3-(4,6-dimethoxypyrimidin- 2-yl)-1-[3-(N-methylsulfonyl-N-methylamino-pyridin- 2-yl)-sulfonyl]-urea.

8. A method of controlling undesired plants in crops which comprises applying to the plants, parts of the plants, seeds of the plants or the area under cultivation an effective amount of at least one herbicidal active substance selected from the group consisting of phenoxyphenoxy- and heteroaryloxyphenoxyalkanecarboxylic acid derivatives and sulfonylureas, in combination with an effective amount of at least one safener compound of formula (I) as claimed in claim 1.

9. A method as claimed in claim 8, wherein in the safener of formula (I)

X is an oxygen atom,

R is $C_1$–$C_4$-alkoxy or hydroxyl,

Z is halogen or methyl and n is an integer of from 0 to 2.

10. A method as claimed in claim 9, wherein the herbicide is selected from the group consisting of fenoxapropethyl, fenoxaprop-P-ethyl.

11. A method as claimed in claim 9, wherein the herbicide is selected from the group consisting of pyridinylsulfonylurea herbicides.

12. A method as claimed in claim 9, wherein the herbicide is 3-(4,6-dimethoxypyrimidin-2-yl)- 1-[3-(N-methylsulfonyl-N-methylamino-pyridin- 2-yl)-sulfonyl]-urea.

13. A method of protecting crop plants against phytotoxic effects of herbicides selected from the group consisting of phenoxyphenoxy- and heteroaryloxyphenoxyalkanecarboxylic acid derivatives and sulfonylureas which comprises applying to the plants, parts of the plants, seeds of the plants or the area under cultivation an effective amount of at least one safener compound of formula (I) as claimed in claim 1.

14. A method as claimed in claim 13, wherein in the safener of formula (I)

X is an oxygen atom,

R is $C_1$–$C_4$-alkoxy or hydroxyl,

Z is halogen or methyl and n is an integer of from 0 to 2.

15. A method as claimed in claim 14, wherein the herbicide is selected from the group consisting of fenoxapropethyl, fenoxaprop-P-ethyl.

16. A method as claimed in claim 14, wherein the herbicide is selected from the group consisting of pyridinylsulfonylurea herbicides.

17. A method as claimed in claim 16, wherein the herbicide is 3-(4,6-dimethoxypyrimidin-2-yl)- 1-[3-(N-methylsulfonyl-N-methylamino-pyridin- 2-yl)-sulfonyl]-urea.

* * * * *